(12) United States Patent
Decourcelle et al.

(10) Patent No.: US 8,316,652 B2
(45) Date of Patent: Nov. 27, 2012

(54) SYSTEM AND METHOD FOR WHOLE-BODY CRYOTHERAPY

(76) Inventors: Olivier Marcel Maurice Decourcelle, Paris (FR); Gilles Barette, Montfermeil (FR)

(*) Notice: Subject to any disclaimer, the term of this patent is extended or adjusted under 35 U.S.C. 154(b) by 845 days.

(21) Appl. No.: 12/517,911

(22) PCT Filed: Nov. 27, 2007

(86) PCT No.: PCT/FR2007/052407
§ 371 (c)(1), (2), (4) Date: Jun. 5, 2009

(87) PCT Pub. No.: WO2008/068441
PCT Pub. Date: Jun. 12, 2008

(65) Prior Publication Data
US 2010/0313579 A1 Dec. 16, 2010

(30) Foreign Application Priority Data
Dec. 7, 2006 (FR) ...................... 06 10658

(51) Int. Cl.
*F17C 13/08* (2006.01)
(52) U.S. Cl. ................ 62/53.2; 62/60; 62/239
(58) Field of Classification Search ............. 62/53.2, 62/60, 239, 259.3, 371
See application file for complete search history.

(56) References Cited

U.S. PATENT DOCUMENTS

| | | | |
|---|---|---|---|
| 3,421,336 A * | 1/1969 | Lichtenberger et al. | 62/52.1 |
| 4,060,400 A | 11/1977 | Williams | |
| 4,498,306 A | 2/1985 | Tyree, Jr. | |
| 4,576,010 A * | 3/1986 | Windecker | 62/64 |
| 5,077,980 A | 1/1992 | Weber | |
| 5,161,848 A | 11/1992 | Lutton | |
| 6,378,319 B1 | 4/2002 | Mani | |
| 2002/0129613 A1 | 9/2002 | Viegas et al. | |

FOREIGN PATENT DOCUMENTS

| | | |
|---|---|---|
| EP | 0 371 072 B1 | 6/1990 |
| WO | 2006/045124 | 4/2006 |

OTHER PUBLICATIONS

International Search Report dated Jul. 4, 2008, from corresponding PCT application.

* cited by examiner

*Primary Examiner* — Melvin Jones
(74) *Attorney, Agent, or Firm* — Young & Thompson

(57) ABSTRACT

The present invention relates to a system, and to a method for installation of the system, for whole-body cryotherapy applicable to humans or animals at a temperature of the order of −110° C. According to the invention, the treatment chamber and the refrigerating elements, or at least one of these two elements, are mounted on at least one mobile or transportable self-supporting structure, in a way that permits use from the self-supporting structure. It also relates to a whole-body cryotherapy system equipped with pre-chambers at intermediate temperatures, defining a modifiable or removable two-way path between the treatment chamber and the outside, and including elements for local cryotherapy. It also relates to such a system divided into several separable modules.

20 Claims, 3 Drawing Sheets

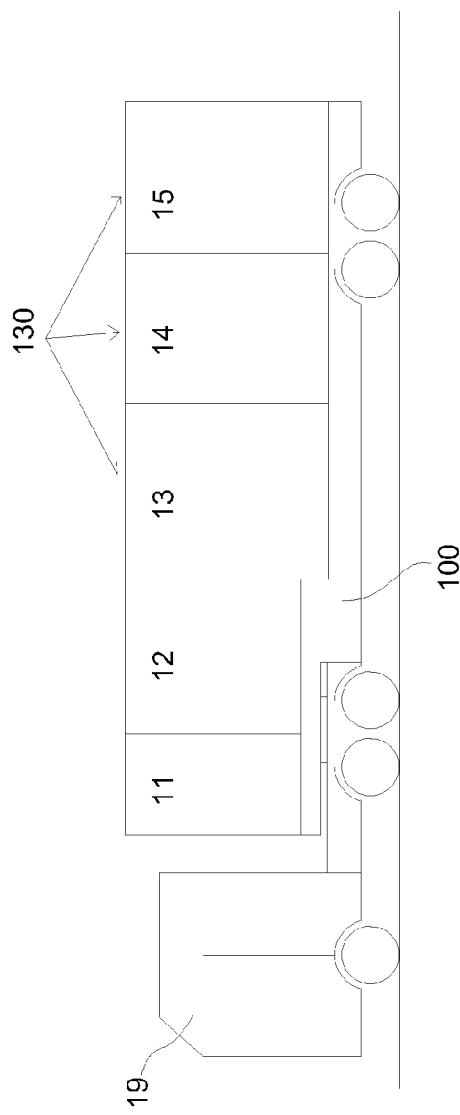
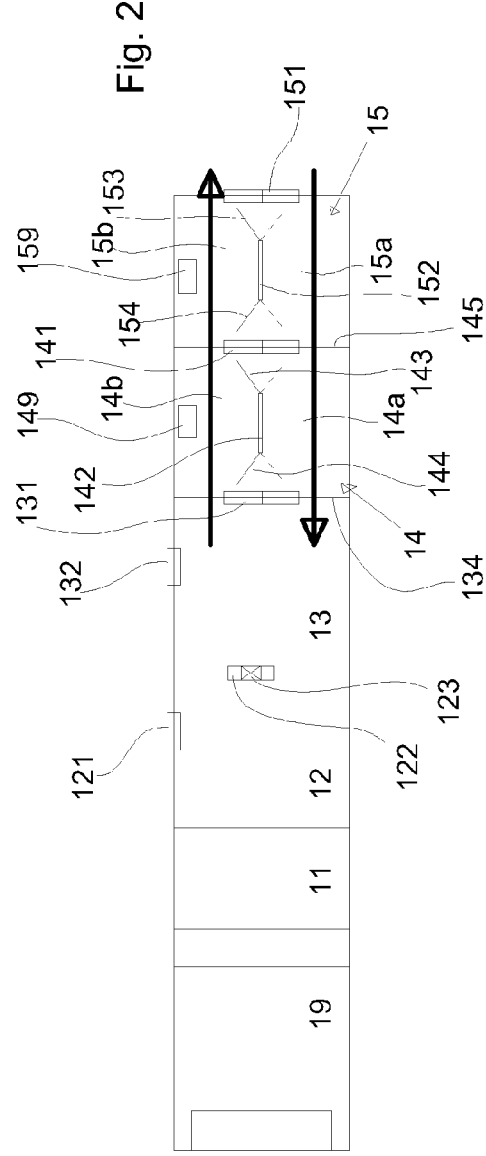

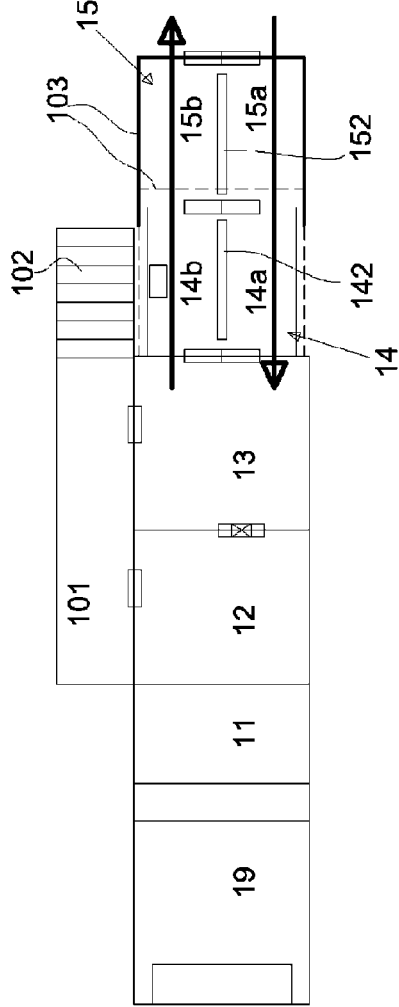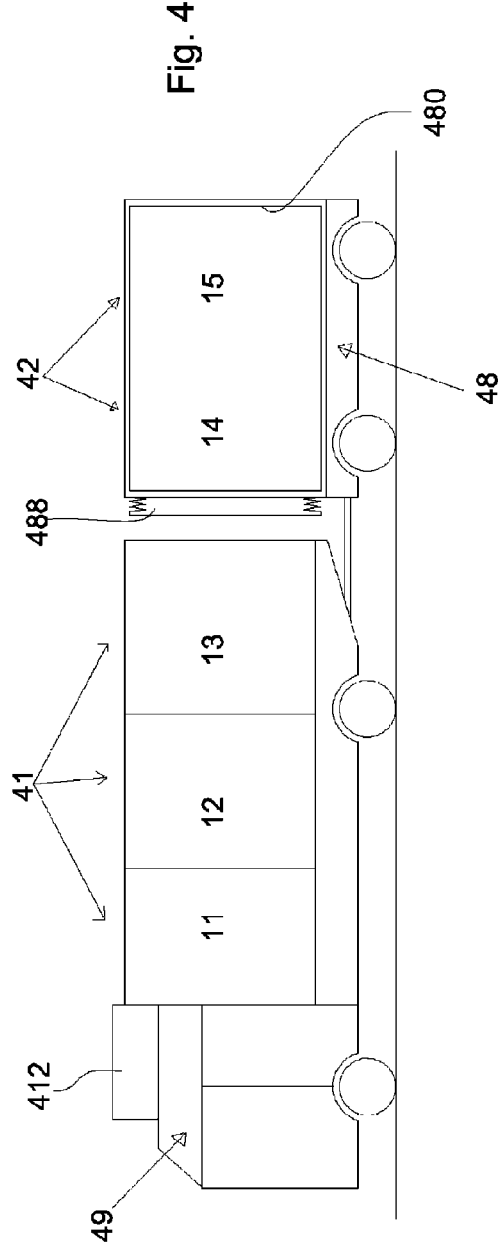

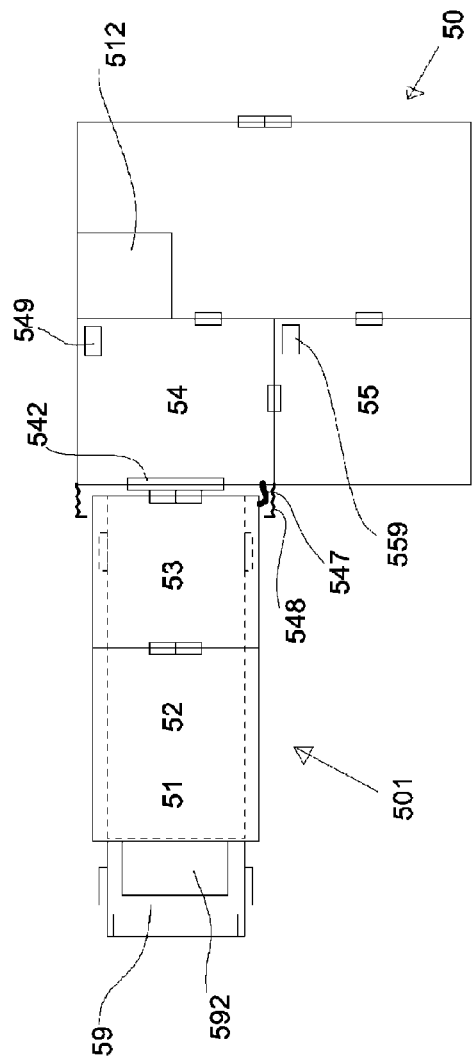
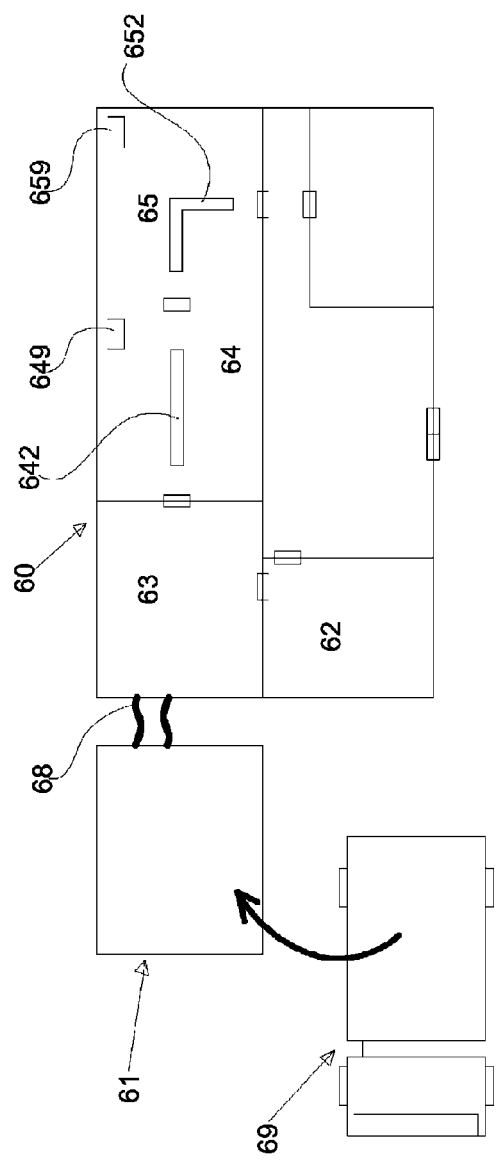

SYSTEM AND METHOD FOR WHOLE-BODY CRYOTHERAPY

The present invention relates to a system for whole-body cryotherapy which can be applied to human or animal subjects as well as a method for the setting up thereof; this system comprises a treatment chamber as well as refrigeration means capable of bringing the atmosphere of this treatment chamber to a temperature below −80° C. or maintaining it at that temperature. According to the invention, this treatment chamber and said refrigeration means, or at least one of these two elements, are mounted on at least one self-supporting mobile or transportable structure, in order to allow operation from said self-supporting structure.

It relates moreover to a whole-body cryotherapy system provided with antechambers at intermediate temperatures, defining a dual route between the treatment chamber and the outside which can be modified or removed, and comprising local cryotherapy means.

It also relates to such a system distributed over several modules which can be separated.

The principal field of the invention is that of extremely low-temperature treatments, mainly applied to living things, in particular at temperatures below −80° C., for example between −100° C. or −120° C., often in the region of −110° C.

Although usually known as "cryotherapy", such treatment can have other than therapeutic purposes, such as well-being, aesthetics or steadiness of physical performance.

In the last few years, studies have demonstrated that exposing the body to extremely low temperatures for a short duration comprised between 0.5 minute and a few minutes allows a bodily reaction to be obtained which produces effects over an extended period or even permanently.

Such treatments are based on a direct exposure of the skin to the air at a very low temperature. Over short periods, the core temperature is not affected and only the temperature at the surface of the body drops, to around +25° C.

Therefore, results have been obtained in the management of certain generalized and chronic disorders in the fields of traumatology, rheumatology and neurology.

These types of treatment can also be used to improve a person's general well-being by reactivating their metabolism. Certain results can also be obtained aesthetically, for example by acting on the condition or appearance of the skin.

A major interest is currently seen in the field of sport, in particular competition or high-level sport. Research shows that recovery after intense exertion becomes more effective and quicker, and fragilization or risk of injury are reduced.

Over an extended period, in training but also in a competition extending over several days or weeks, physical capacity is also regularized or made more steady.

The currently existing systems are installed in certain specialized centres of the therapeutic type or in certain sports complexes or those specialized in sports medicine. Such an installation is based on a thermally-insulated chamber, cooled by liquid nitrogen or by a special compressor, for example with three-stage cascade compression.

Such compressors are based on a very specialized technology, and differ significantly from standard refrigeration installations, which at best are only capable of reaching approximately −60° C. and more often only −40° C. This type of compressor, which has only recently been developed, uses special fluids and involves a high level of consumption and high cost.

Moreover, notwithstanding, the time needed to get to the required temperature is still considerable, as going from −60° C. to the treatment temperature of −110° C. can require between three and four hours' operation.

Currently there are few examples of such installations and they are very costly, which means that such equipment is out of the question for many low-budget sites and/or those with an insufficiently high level of use.

Certain systems are provided with one or two antechambers, in which the temperature is kept at intermediate temperatures, and through which the subject's pass/es in order to gain access to, or leave, the treatment chamber.

Such systems are described in European patent EP 0,371,072, and are offered for sale by companies such as Zimmer Elektromedizin or Cryo Medizintechnik in Germany or Xolod in Ukraine.

In certain situations, the capacity of a system can sometimes prove to be insufficient, even with two antechambers, for example for treating all the members of both teams within the optimum period after a team sports meeting, i.e. at least 22 players in football or 30 in rugby. Thus the capacity of a two-room installation is given for 10-12 persons/hour and up to 20-25 persons/hour according to the information from Xolod.

A purpose of the invention is to overcome all or part of these drawbacks, and in particular:
- to increase the flexibility of such a system in use;
- to facilitate access to such treatments for occasional or one-off users or sites;
- to improve the performance of this type of treatment, by reducing the time periods between the physical exertion and application of the treatment;
- to reduce the costs of access to such treatments and make better use of the investment put into this type of system;
- to reduce the preparation time of such a system;
- to increase the capacity of such a system;
- to better integrate this type of treatment within the framework of the different existing types of physiotherapy, and to optimize combinations thereof.

To this end, the invention relates to a whole-body cryotherapy system for human or animal subjects, comprising At least one treatment chamber having dimensions sufficient to contain at least one subject to be treated, as well as refrigeration means capable of bringing the atmosphere of said treatment chamber to, or maintaining it at, a temperature below −80° C.

According to the invention, said treatment chamber and said refrigeration means, or at least one of these two elements, are mounted on at least one self-supporting mobile or transportable structure, so as to allow operation from said self-supporting structure. This self-supporting structure can be for example a module or a container containing these elements or a platform supporting these elements.

More particularly, the self-supporting structure is integrated with a road vehicle or trailer, or comprises means of attachment to such a vehicle or trailer. This self-supporting structure can also comprise gripping means allowing said self-supporting structure to be handled by lifting or handling means, which can themselves be fixed on such a vehicle or trailer.

It is thus possible to move the cryotherapy system, in order to position it temporarily and as a one-off, on the site where it is required. This system can be moved in one or more parts, for example in modules or container units, which can be fixed or placed together. The modules constitute cells which can be assembled together and comprise the connections necessary to make the unit operational in a simple manner, while avoiding or reducing the assembly or adjustment operations when putting it into service.

It thus becomes possible to offer a service which is mobile on demand, anywhere, by prior notice from a few hours to a few days.

This type of service can be aimed at various users who hitherto have not had the need or the means to invest in an on-site installation, for example small sports organizations for a few specific occasions, at a cost corresponding to such a use.

Moreover, it is thus possible to carry out such treatment immediately after exertion, for example at the end of a sporting event, even if the event takes place on a site where no plant is in place. In fact, the effect on recovery and consistency of performance is improved if the treatment is applied within a relatively short period after exertion, which does not always allow the subject's to consider travelling to a site having such equipment.

By providing for a multiplicity of occasional or one-off clients, it is also easier to recoup the investment that such a system represents, despite possible extra construction cost that may be incurred by the mobile nature of said system.

Advantageously, the treatment chamber communicates with the outside by means of one or more successive antechambers, each having dimensions sufficient to contain at least one subject to be treated, the respective atmospheres of which are brought to, or maintained at, one or more intermediate temperatures between the outside temperature and the temperature of the treatment chamber.

According to the invention, the system can comprise local cryotherapy means which can be used from inside at least one antechamber. By applying such a local therapy on leaving the treatment chamber, its effects are thus potentiated by having previously passed through $-110°$ C.

The skin temperature of a human subject in an environment at $+20°$ C. is normally approximately $+32°$ C. The local cryotherapy consists of cooling the skin by at least $15°$ C. in order to initiate a vasodilatation reaction from the body core. After the exposure to $-110°$ C., the surface temperature has already dropped, for example to around $+25°$ C. A local cryotherapy is applied in an antechamber at $-60°$ C. or $-10°$ C. to bring the skin to the temperature triggering vasodilatation, for example around $+17°$ C. The effects of this local cryotherapy are more effective due to the cold atmosphere and the reaction already initiated in the body of the subject, and will also be obtained more rapidly due to the already lowered surface temperature. By way of example, such a local treatment which would take approximately 10 minutes in an environment at $+20°$ C. can require only approximately one minute in an environment at $-10°$ C. and after exposure to $-110°$ C.

Advantageously, at least one antechamber can comprise a physical separation device defining at least two separate routes between on the one hand at least one opening communicating with the adjacent space having a temperature below the temperature of said antechamber, and on the other hand at least one opening communicating with the adjacent space having a temperature above the temperature of said antechamber.

It is thus possible to use one of these routes as an entry route to the treatment chamber and the other as an exit route. Such physical separation makes organization of the flow of treated subjects more natural and more effective. By separating the entering and leaving subjects in one or both of the antechambers, it is also possible to increase the overall capacity of the system by having new subjects enter each antechamber at the same time as others leave it, avoiding the risk of their becoming confused, and limiting the risks of jostling and contact with the walls. It is thus possible to use the treatment chamber closer to its theoretical maximum capacity. The capacity obtained can then exceed 30 or 40 persons/hour for a 2-minute exposure in a 5-person chamber.

In certain embodiments of the invention, the system comprises at least two separable modules of which at least one is mounted on a mobile or transportable self-supporting structure, so as to allow operation from said self-supporting structure, one of said modules comprising at least the treatment chamber, and the other of said modules comprising at least the refrigeration means or at least one antechamber.

Such modules can be transported on different vehicles, or distributed on a vehicle and its trailer, which makes the system occupy less space and its transportation more versatile.

Thus it is also possible to move the different elements separately according to need.

In one of these embodiments, the refrigeration means are mounted on a mobile or transportable self-supporting structure. The system then comprises connection means for connecting said refrigeration means detachably to one or more treatment chambers constructed or transported independently of said refrigeration means.

Such a configuration makes it possible to put the treatment chamber in position in advance and gain time on the installation. It also makes it possible to install several, possibly permanent, treatment chambers in different places. These different treatment chambers can then be used with a single refrigeration module introduced at a convenient time, its cost thus being more easily recouped or a return on investment achieved.

In another of these embodiments, the refrigeration means and the treatment chamber are mounted on one or more mobile or transportable self-supporting structures, and the system can comprise connection means for detachably connecting said treatment chamber to one or more antechambers constructed or transported independently of said refrigeration means.

The antechambers can thus form part of fixed installations, such as changing-rooms or a physiotherapy centre. Cryotherapy can thus be carried out in a place where the means and personnel necessary for other treatments, complementary or useful to the same subjects, are grouped together. These other treatments can in particular comprise electrotherapy, light therapy, laser treatment, massages, hydrotherapy and other physiotherapy techniques.

In embodiments which can be combined with all or part of those mentioned above, the system comprises moreover second refrigeration means, for example a refrigeration unit using a more standard and less costly technology.

These second means can ensure the operation of local cryotherapy means. They can also provide all or part of reaching or maintaining the temperature of at least one antechamber at a temperature above that of the treatment chamber. They can also provide an auxiliary or preparation for reaching or maintaining the temperature of the treatment chamber.

For these requirements, the maximum performance levels of the main refrigeration means are not always necessary. Such secondary means are thus more economical and simpler to operate, can be more reliable and more robust, requiring less maintenance, and more capable of operating during transportation.

Thus the invention also relates to a method for preparing such a whole-body cryotherapy system.

This method comprises a stage of transporting the refrigeration means and/or the treatment chamber to a chosen site for one-off or non-permanent use, followed by a stage of bringing the treatment chamber to temperature.

Other features and advantages of the invention will become apparent from the detailed description of embodiments that are in no way limitative, and the attached drawings, in which:

FIG. 1 is a side-view diagram showing a system according to the invention mounted on a semi trailer;

FIG. 2 is a top-view diagram showing the organization of a system according to the invention mounted on a heavy goods vehicle;

FIG. 3 is a top-view diagram showing the organization of a system according to the invention in a variable-geometry embodiment;

FIG. 4 is a side-view diagram showing a system according to the invention mounted on a carrier vehicle and separate trailer;

FIG. 5 is a top-view diagram showing an embodiment of the invention with mobile refrigeration means, fixed treatment chamber and antechambers;

FIG. 6 is a top-view diagram showing an embodiment of the invention with mobile refrigeration means and a fixed treatment chamber;

FIG. 1 and FIG. 2 show an embodiment of the invention where all the elements of the cryotherapy system are permanently and operationally mounted on a heavy goods vehicle, here in the form of a semi trailer 100 constituting the self-supporting structure and adaptable to a tractor unit 19. The articulated vehicle principle allows a certain flexibility of use and economy of investment due to the fact that the tractor unit is removable and interchangeable. A close embodiment could also be realized based on a coach-type vehicle, for greater compactness on the road and a presentation more associated with tourism and comfort.

The on-board components include, starting from forward of the operational part: a technical compartment 11 grouping together the special refrigeration compressor and an electricity generator unit, the control room 12, then the extreme-cold chamber 130.

The refrigeration and control elements can typically be of the same type as in the existing fixed installations, such as those supplied for example by Cryo Medizin and/or Bock.

The technical compartment 11 comprises an electricity generator unit supplying all or part of the system, in particular when travelling. It also comprises the refrigeration means, for example a special three-stage compressor making it possible to obtain the temperature of −110° C. in the treatment chamber.

The refrigeration means are suspended by at least one suspended structure, mounted so as to allow operation from said suspended structure, thus limiting the vibrations that they receive during transportation.

Such a suspended structure is for example a frame supporting the set of elements of the three-stage compressor and mounted on the self-supporting structure 100 by shock absorption means of a known type, such as a deformable material of the high-density foam type, or a closed-cell foam, or rubber silentblocs, a system of springs plus hydraulic shock-absorbers or a hydraulic or oleopneumatic suspension.

In the case of a system with separable or demountable modules in containers as described below, the suspension means can also be situated outside the self-supporting structure, i.e. for example between the vehicle and the container.

The control room 12 comprises all the means for controlling and monitoring the operation of the system and for monitoring the treatment. It is provided with an external access door 121 and a thermally-insulated door 122 communicating with the treatment chamber 13 and provided with a window 123 allowing a view into the inside of the treatment chamber 13.

Here, the extreme-cold chamber is a type called "three-stage airlock" comprising three successive thermally-insulated cubicles 13, 14 and 15, intercommunicating by openings provided with thermally-insulated doors.

Certain embodiments described here can however perfectly well be combined with a "two-stage airlock" or "single-stage airlock" architecture.

Entry from the outside takes place via cubicle 15, by an external door 151, opening onto a platform or provided with an access stairway when in use. This cubicle 15 constitutes a first antechamber and forms an intermediate-temperature stage, with an internal temperature of −10° C. when in operation.

Access can be gained from this first antechamber 15 via a door 141 to another cubicle constituting a second antechamber 14, where an internal temperature of −60° C. prevails. Access can be gained from this second antechamber 14 to another cubicle constituting the treatment chamber 13. This treatment chamber 13 is also provided with an external door 132 which can be used for technical access or as an emergency door.

As shown in FIG. 2, the first antechamber 15 and the second antechamber 14 are each subdivided into two parts 15a, 15b and respectively 14a, 14b by a physical division, for example a partition 152, 142 or possibly a simple guardrail.

In the first antechamber 15, this partition 152 runs from the external door 151 to a door 141 communicating with the second antechamber 14. In the second antechamber 14, this partition 142 runs from this same access door 141 to the door 131 communicating with the treatment chamber 13.

This partition 152 is provided at each of its ends with a moveable barrier 153 and 154, which can be controlled from the control room 12. These barriers 153 and 154 can also be designed to move automatically or be moved manually in order to allow access to each of the parts 15a respectively 15b of the antechamber 15 only via one of the access doors 151 respectively 141.

Similarly, the partition 142 of the second antechamber 14 is provided at each of its ends with a moveable barrier 143 and 144, which can be controlled from the control room 12. These barriers 143 and 144 can also be designed to move automatically or be moved manually in order to allow access to each of the parts 14a respectively 14b of the antechamber 14 only via one of the access doors 141 respectively 131.

This subdivision by the partitions 152 and 142, as well as the operation of the corresponding barriers, makes it possible to organize movement in a single direction between the outside and the treatment chamber via the first parts 15a and 14a of the two antechambers in the entry direction, and via the second parts 14b and 15b of these same antechambers in the exit direction.

In the first antechamber 15 and the second antechamber [14], or only one of the two, preferably in the part 14b, 15b acting as exit route, provision is made for means of local cryotherapy treatment 149 and 159, for example of a known type with a moveable nozzle spraying cold air between −20° C. and −45° C. These means can thus be used for the specific treatment of certain parts of the body such as the joints or localized muscular conditions, the effects of which means being reinforced and facilitated by being combined with the whole-body treatment.

In a variant which is not shown, these various doors 151, 141 and 131 are sufficiently wide, or open in two parts, or each comprise two separate doors, to allow movement in both directions simultaneously with no barrier to be maneuvered.

Moreover, one or more partitions providing at least one physical separation device between two antechambers or inside one antechamber are moveable or detachable.

It is thus possible to change easily from one configuration to another according to need, for example by removing partitions or divisions in order to increase the available space and treat subjects with a particularly large space requirement, for example racehorses.

A possible configuration thus consists of removing partitions 142 and 152 from each of the antechambers 14 and 15, in order to increase the available width or to facilitate maintenance.

The separation between the first antechamber 15 and the second antechamber 14 can also be moveable or detachable, making it possible to obtain a single antechamber of greater length. By removing the partition 145 between the first antechamber 15 and the second antechamber 14, a "two-stage airlock" type system is thus obtained.

The external door 151 and the access door 131 to the treatment chamber are provided with sufficient dimensions to allow such bulky subjects to pass, for example by using two independent swing doors.

The separation between the second antechamber 14 and the treatment chamber 13 can also be moveable or detachable. By removing the partition 134 between the second antechamber 14 and the treatment chamber 13, a "single-stage airlock" type system is thus obtained, having a greater capacity.

FIG. 3 shows an embodiment where the system comprises at least one moveable part 101, 103 allowing modification of the horizontal dimensions of at least one element that it supports. Such a variable-geometry configuration, which can for example be folded out or extended, makes a sufficient space available when stationary and in use, without creating an excessively large bulk during transport or exceeding any size or road traffic regulations.

In this example, the semi trailer 100 comprises a side platform 101 capable of sliding under the floor of cubicles 12 and 13 or capable of being folded back onto the outside of their side wall. This platform 101 is provided with a folding stairway 102 which when stationary allows convenient and safe access to the control room 21 and the external door of the treatment chamber 13.

In its rear part, the semi trailer 100 comprises a structure 103 fitting around the external walls of the second antechamber 14, and capable of sliding toward the rear in order to free a space constituting the first antechamber 15, in which the detachable partitions 152 and 142 can then be installed.

Such a variable geometry can of course be combined with other embodiments of the invention, for example with a single vehicle, a demountable container or an independent trailer.

FIG. 4 shows an embodiment of the invention where the system is distributed over two separate modules capable of being interconnected for operation.

A first module 41 is carried by a heavy goods vehicle 49 and a second module 42 is carried by a trailer 48, which can be pulled by this same vehicle 49 or be moved independently.

In this example, the main vehicle 49 carries the technical compartment 11, the control room 12 and the treatment chamber 13, and the trailer 48 carries the two antechambers 14 and 15. Either one of the two modules 41 and 42 comprises moreover connection means 488 allowing a simple and reversible connection of the different fluids or data, as well as thermal protection and insulation of the passage between different low-temperature zones 13, 14.

During the transport stage, the method can also include a pre-cooling of at least the treatment chamber by second refrigeration means capable of operating during travel or during stopovers on said travel.

This pre-cooling is provided by second refrigeration means 412 capable of operating while travelling or by connection to the mains supply during stopovers, for example a standard compressor unit as used in refrigerated transport.

The time for reaching the final temperature after arrival or installation on site is thus reduced.

FIG. 5 shows an implementation of the system in an embodiment comprising the treatment chamber mounted without antechambers on a vehicle 59.

The vehicle has on board a technical compartment 51, the control room 52 and a treatment chamber 53. This vehicle is positioned in front of an antechamber 54 forming part of a fixed installation, for example in a building 50. The system comprises connection means, for example an electrical and data link 547 and an extensible airlock 548, which can be mounted on the outside of the antechamber 54 or behind the treatment chamber 53.

According to the invention, the transport stage is then followed by a stage of connection or securing the treatment chamber to at least one antechamber constructed or transported independently of the treatment chamber, thus allowing the use of installations existing on site or supplied previously.

The system also comprises on-board second refrigeration means 592, capable of operating while travelling or during stopovers, in order to provide pre-cooling of the treatment chamber 53, and thus reducing the preparation time of the unit after arrival of the vehicle.

The installation 50 also comprises a technical compartment 512 comprising fixed second refrigeration means 512, which make it possible to provide cooling or pre-cooling of the second antechamber 54, as well as cooling the first antechamber 55 and the operation of the local treatment devices 549 and 559 of the first and second antechambers 55 and 54.

FIG. 6 shows an embodiment of the invention where the system comprises a module 61 including the specific refrigeration means. This module is mounted on a vehicle 69, for example in a self-supporting container which can be unloaded using a crane which is carried on-board or not.

This module is brought close to an installation which can itself be wholly or partially fixed or mobile, for example integrated into a building 60. This installation comprises a treatment chamber 63 and a control room 62 to which the refrigeration means of the module 61 are connected by connection means 68 for fluids and data. The refrigeration means of the module 61 can also comprise a moveable part, for example comprising a condenser unit, permanently connected to the remainder of said module, and which can be moved over a short distance in order to be coupled to, or introduced into or close to the treatment chamber 13.

The installation 60 also comprises a technical compartment 612 comprising second refrigeration means, which make it possible to provide pre-cooling of the treatment chamber 63, and the second antechamber 64, as well as cooling the first antechamber 65 and the operation of the local treatment devices 649 and 659 of the first and second antechambers 65 and 64.

In the various embodiments of the invention, each module can also, as a variant, either be integrated with a vehicle or trailer or be mounted on a frame or in a container 480 which can be separated from said vehicle or trailer 48.

Of course the invention is not limited to the examples that have just been described and numerous adjustments can be made to these examples without exceeding the scope of the invention.

The invention claimed is:

1. Whole-body cryotherapy system for human or animal subjects, comprising at least one treatment chamber of sufficient dimensions to contain at least one subject to be treated, as well as refrigeration means by compressor capable of bringing the atmosphere of said treatment chamber to a temperature below −80° C. or maintaining it at that temperature, characterized in that said treatment chamber and said refrigeration means, or at least one of these two elements, are mounted on at least one self-supporting mobile or transportable structure and are arranged on said self-supporting structure so as to allow operation from said self-supporting structure.

2. System according to claim 1, characterized in that the self-supporting structure is integrated with a road vehicle or trailer, or comprises means of attachment to such a vehicle or trailer, or gripping means allowing the handling of said structure by lifting or handling means.

3. System according to claim 1, characterized in that the refrigeration means are suspended by at least one suspended structure, mounted so as to allow operation from said suspended structure.

4. System according to claim 1, characterized in that the treatment chamber communicates with the outside by means of one or more successive antechambers, each having dimensions sufficient to contain at least one subject to be treated, and the respective atmospheres of which are brought to, or maintained at, one or more intermediate temperatures between the outside temperature and the temperature of the treatment chamber.

5. System according to claim 4, characterized in that it comprises local cryotherapy means which can be used from within at least one antechamber.

6. System according to claim 4, characterized in that at least one antechamber comprises a physical separation device defining at least two separate routes between, on the one hand, at least one opening communicating with the adjacent space having a temperature below the temperature of said antechamber, and on the other hand, at least one opening communicating with the adjacent space having a temperature above the temperature of said antechamber.

7. System according to claim 4, characterized in that it comprises one or more moveable or detachable partitions providing at least one physical separation device between two antechambers or within one antechamber.

8. System according to claim 1, characterized in that it comprises at least two separable modules at least one of which is mounted on a mobile or transportable self-supporting structure, in order to allow operation from said self-supporting structure, one of said modules comprising at least the treatment chamber, and the other of said modules comprising at least the refrigeration means or at least one antechamber.

9. System according to claim 2, characterized in that the road vehicle or the road trailer comprises at least one moveable part allowing a modification of the horizontal dimensions of at least one element that it supports.

10. System according to claim 8, characterized in that the refrigeration means are mounted on a mobile or transportable self-supporting structure, said system comprising connection means for connecting said refrigeration means detachably to one or more treatment chambers constructed or transported independently of said refrigeration means.

11. System according to claim 8, characterized in that the refrigeration means and the treatment chamber are mounted on one or more mobile or transportable self-supporting structures, said system comprising connection means for connecting said treatment chamber detachably to one or more treatment chambers constructed or transported independently of said refrigeration means.

12. System according to claim 1, characterized in that it comprises moreover second refrigeration means ensuring operation of the local cryotherapy means; or ensuring all or part of bringing the temperature of at least one antechamber to a temperature above that of the treatment chamber or maintaining it at that temperature; providing additional means for reaching or maintaining the temperature of the treatment chamber or preparation therefor.

13. Method for the preparation of a system according to claim 1, characterized in that it comprises a stage of transporting the refrigeration means and the treatment chamber, or at least the refrigeration means, to a site chosen for a one-off or non-permanent use, said transport stage being at least followed by a stage of bringing the temperature of the treatment chamber to its operating temperature.

14. Method according to claim 13, characterized in that the transport stage includes a pre-cooling of at least the treatment chamber by the second refrigeration means capable of operating during travel or during stopovers on said travel.

15. Method according to claim 13, characterized in that the transport stage is followed by a stage of connecting or securing the treatment chamber to at least one antechamber constructed or transported independently of the treatment chamber.

16. Method according to claim 14, characterized in that the transport stage is followed by a stage of connecting or securing the treatment chamber to at least one antechamber constructed or transported independently of the treatment chamber.

17. System according to claim 5, characterized in that at least one antechamber comprises a physical separation device defining at least two separate routes between, on the one hand, at least one opening communicating with the adjacent space having a temperature below the temperature of said antechamber, and on the other hand, at least one opening communicating with the adjacent space having a temperature above the temperature of said antechamber.

18. System according to claim 5, characterized in that it comprises one or more moveable or detachable partitions providing at least one physical separation device between two antechambers or within one antechamber.

19. System according to claim 6, characterized in that it comprises one or more moveable or detachable partitions providing at least one physical separation device between two antechambers or within one antechamber.

20. System according to claim 9, characterized in that the refrigeration means are mounted on a mobile or transportable self-supporting structure, said system comprising connection means for connecting said refrigeration means detachably to one or more treatment chambers constructed or transported independently of said refrigeration means.

* * * * *